United States Patent
Sakai et al.

[11] Patent Number: 6,126,312
[45] Date of Patent: Oct. 3, 2000

[54] MOISTURE SENSITIVE ELEMENT AND METHOD OF MANUFACTURING THE SAME

[75] Inventors: Yoshiro Sakai; Masanobu Matsuguchi; Hiroyuki Hara, all of Ehime; Sachiko Suzuki; Nobuaki Honda, both of Tokyo, all of Japan

[73] Assignee: Yamatake-Honeywell Co., Ltd., Japan

[21] Appl. No.: 09/071,280

[22] Filed: May 1, 1998

[30] Foreign Application Priority Data

May 2, 1997  [JP]  Japan ................................... 9-114683

[51] Int. Cl.$^7$ .......................... G01N 25/56; G01N 7/16; G01N 19/10; G01R 27/28
[52] U.S. Cl. .................. 374/28; 73/73; 73/29.01; 73/335.04; 324/664
[58] Field of Search ................ 374/27, 28, 159, 374/160, 461, 162, 54; 73/335.02, 335.03, 335.04, 335.05, 73, 29.01; 324/664, 694

[56] References Cited

U.S. PATENT DOCUMENTS

| | | | |
|---|---|---|---|
| 4,245,506 | 1/1981 | Meiklejohn | 73/336 |
| 4,683,258 | 7/1987 | Itoh et al. | 524/434 |
| 4,696,796 | 9/1987 | Oka et al. | 73/335.02 |
| 4,920,451 | 4/1990 | Sakai et al. | 73/335.02 |
| 5,079,272 | 1/1992 | Allegrezza et al. | 521/134 |
| 5,136,274 | 8/1992 | Shimomura et al. | 73/335.05 |
| 5,296,819 | 3/1994 | Kuroiwa et al. | 324/664 |
| 5,317,274 | 5/1994 | Nakagawa et al. | 324/664 |
| 5,533,393 | 7/1996 | Bonne et al. | 73/355.02 |
| 5,546,802 | 8/1996 | Yoshimura et al. | 73/335.05 |
| 5,767,687 | 6/1998 | Geist | 324/664 |

FOREIGN PATENT DOCUMENTS

| | | | |
|---|---|---|---|
| 24 08 902 | 2/1974 | Germany . | |
| 26 10 266 | 3/1976 | Germany | G01N 27/14 |

OTHER PUBLICATIONS

Patent Abstracts of Japan, vol. 008, No. 065, (p–263). Mar. 27, 1984.
"Porous Poly (Vinyl Alcohol) Film" by S. Hayashi et al., Journal of Colloid and Interface Science vol. 77. No. 1, Sep. 1980, p. 6.

*Primary Examiner*—Diego Gutierrez
*Assistant Examiner*—Jeanne-Marguerite Goodwin
*Attorney, Agent, or Firm*—Blakely Sokoloff Taylor & Zafman

[57] ABSTRACT

A moisture sensitive element in which a functional film is formed in contact with opposing electrodes arranged on a substrate. The element includes a mechanism for measuring the temperature of the functional film. The functional film has a porous structure made from a polymer material with hydrophilic properties and includes fine pores. A holding film is formed on inner walls of the pores and made from another polymer material having hydrophobic properties. An electrolytic salt is held within the pores.

6 Claims, 4 Drawing Sheets

MOISTURE SENSITIVE ELEMENT AND METHOD OF MANUFACTURING THE SAME

BACKGROUND OF THE INVENTION

The present invention relates to a moisture sensitive element for measuring a humidity or dew point and a method of manufacturing the same.

Conventionally, moisture in an atmosphere has been regarded as a very important factor having influences on quality. It is being required to measure and control an absolute moisture amount in a variety of fields, e.g., humidity control in a room, moisture control in heat treatments such as carburizing and tempering, humidity adjustment of blast furnace ventilation air, and humidity measurement and adjustment of closed vessels in a warehouse, a storehouse, and a laboratory. Recently, humidity control in semiconductor fabrication factories has become essential, and it is being increasingly demanded to use this technology in the growth control of agricultural products. On the other hand, dew-point measurement in weather conditions is being increasingly required for purposes more closely related to life, e.g., a laundry forecast, as well as a weather forecast. To meet these demands, several absolute moisture amount measuring methods have become popular.

As one method of measuring an absolute moisture amount, a lithium chloride (LiCl) dew-point meter using the deliquescence of lithium chloride measures a dew-point temperature from a change in the electric conductivity of lithium chloride with moisture absorption and a change in the vapor pressure of an aqueous lithium chloride solution with a temperature change. A moisture sensitive element of this meter is manufactured by impregnating a glass fiber tape with an aqueous solution of lithium chloride and spirally winding two parallel thin metal wires as electrodes on the resultant tape. When an AC voltage is applied to the two electrode wires, a current is generated between the electrodes to raise the solution temperature. Simultaneously, moisture in the aqueous solution evaporates to saturate the solution, so the crystal of lithium chloride starts precipitating. When the crystal starts precipitating, the electric resistance of the aqueous solution abruptly increases to reduce the current, and this suppresses the temperature rise. Consequently, a temperature corresponding to the ambient water vapor pressure is held. If the ambient water vapor pressure decreases, the temperature further lowers because the moisture in the aqueous solution evaporates to precipitate the crystal. If the ambient water vapor pressure increases, on the other hand, the moisture is absorbed to break the saturated state, the current increases, and the temperature rises. In this manner the temperature of the aqueous lithium chloride saturated solution is so held as to equilibrate with the ambient water vapor pressure. If this equilibrium temperature is known, the dew-point temperature can be calculated.

If, however, the moisture sensitive element of this lithium chloride dew-point meter is left to stand for long time periods in particularly a high-temperature, high-humidity atmosphere, lithium chloride is rapidly eluted to significantly deteriorate the characteristics. Therefore, it is necessary to perform maintenance and management while periodically replenishing lithium chloride.

As described above, the following state results if the element of the conventional lithium chloride dew-point meter is left to stand for a long time in a high-temperature, high-humidity atmosphere. That is, lithium chloride having strong deliquescence absorbs water vapor in the atmosphere and dissolves in the absorbed water vapor to form an aqueous solution. Usually, a current is supplied to raise the solution temperature to evaporate the moisture. However, if the temperature and humidity of the atmosphere are too high, this moisture evaporation becomes unsatisfactory, and the concentration of the aqueous lithium chloride solution decreases. Consequently, the aqueous lithium chloride solution excessively increases its flowability and flows out from the glass fiber tape holding the solution. When the aqueous lithium chloride solution thus flows out, the amount of lithium chloride used in the moisture sensitive element reduces, and this increases the resistance for the same moisture amount. Accordingly, accurate humidity measurement can no longer be performed.

Conventionally, therefore, maintenance and management must be so performed that the lithium chloride concentration is held at a predetermined concentration by, e.g., periodically replenishing lithium chloride. This makes the management troublesome.

SUMMARY OF THE INVENTION

The present invention has been made to solve the above conventional problem, and has as its object to allow a moisture sensitive element to stably operate over long time periods.

To achieve the above object, a moisture sensitive element according to the present invention is a moisture sensitive element comprising a functional film formed in contact with opposing electrodes arranged on a substrate, and temperature measuring means for measuring a temperature of the functional film, wherein the functional film has a porous structure made from a first polymer material having hydrophilic nature and including a plurality of fine pores, and comprises a holding film formed on inner walls of the pores and made from a second polymer material having hydrophobic nature, and electrolytic salt held in the pores.

Accordingly, the electrolytic salt is confined in a plurality of fine pores in which a hydrophilic group exists. Meanwhile, moisture can freely enter and leave in portions where the electrolytic salt exists.

Also, a method of manufacturing a moisture sensitive element according to the present invention is a method of manufacturing a moisture sensitive element comprising a functional film formed in contact with opposing electrodes arranged on a substrate, and temperature measuring means for measuring a temperature of the functional film, wherein the functional film is formed as follows. That is, a base solution is formed by dissolving a first polymer material having hydrophilic nature in a first solvent having a polarity and capable of dissolving the first polymer material. An emulsion is formed by dispersing a hydrophobic organic material, which is not dissolved in the first solvent, in the base solution. The organic material dispersed in the form of droplets in the emulsion is polymerized to form a suspension in which grains of a second polymer material, which is obtained by the polymerization of the organic material and has hydrophobic nature, are dispersed in the base solution. A coating film is formed by coating a predetermined region on the substrate with the suspension. Moisture in the coating film is partially removed to expose some of the grains to a surface of the coating film. The second polymer material is dissolved by dipping the coating film into a second solvent which does not dissolve the first polymer material and dissolves the second polymer material, thereby forming a porous film by giving the coating film a porous structure having a large number of pores on inner walls formed with a film made from the second polymer material. The porous film is dipped into an aqueous solution of electrolytic salt to impregnate the porous film with the aqueous solution of electrolytic salt, thereby holding the electrolytic salt in the pores constituting the porous film.

That is, a film made from the first polymer material is given a porous structure, and the electrolytic salt is held in a plurality of pores of the porous structure.

DESCRIPTION OF THE PREFERRED EMBODIMENT

An embodiment of the present invention will be described in detail below with reference to the accompanying drawings.

Figure 1:
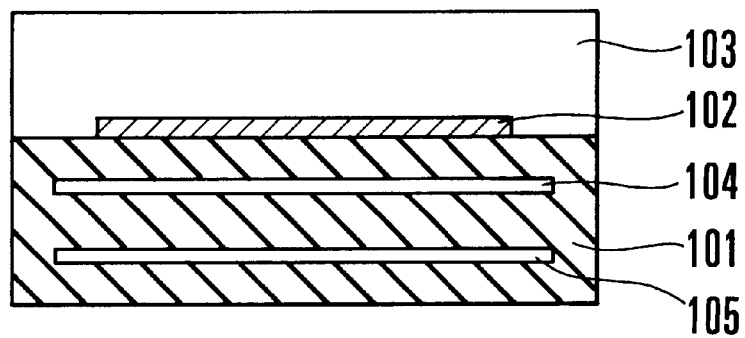
FIG. 1 is a sectional view showing a partial arrangement of a moisture sensitive element according to an embodiment of the present invention.
Figure 2:
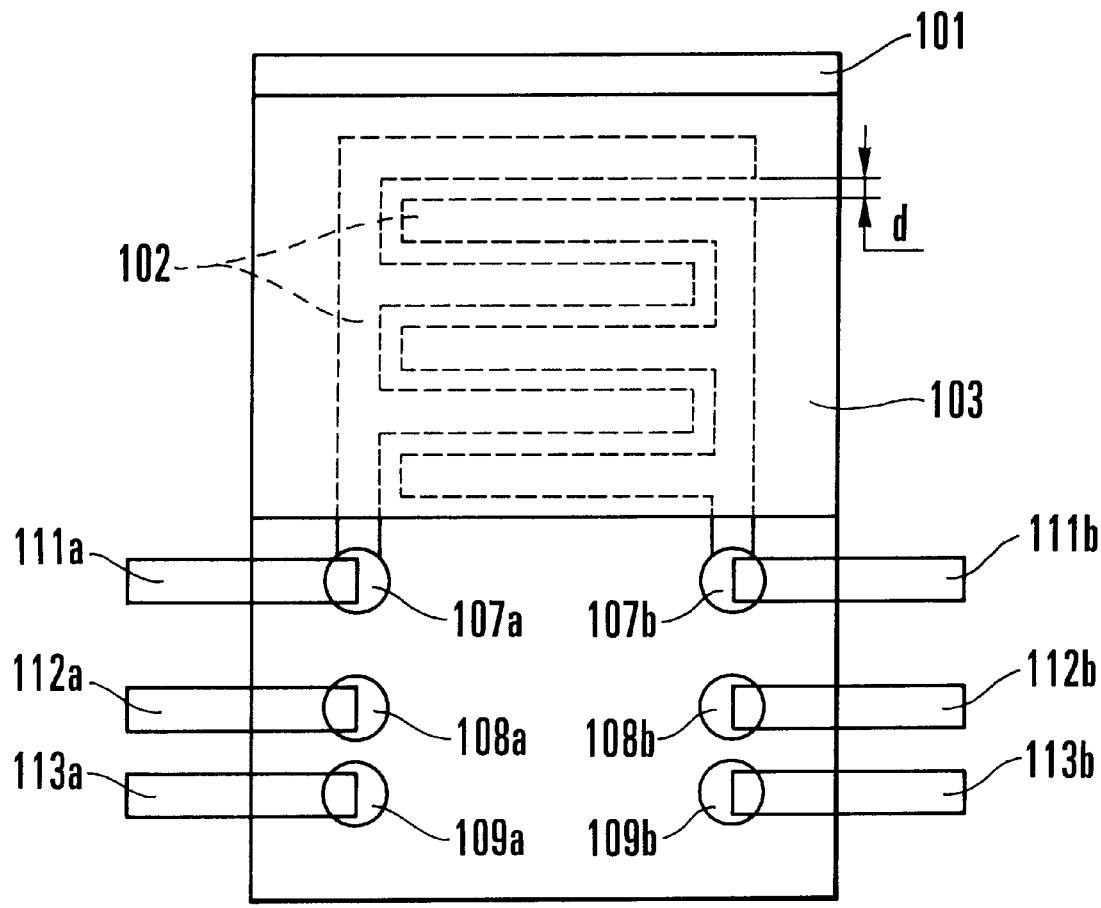
FIG. 2 is a plan view showing part of the arrangement of the moisture sensitive element according to the embodiment of the present invention.

FIGS. 1 and 2 show the arrangement of a moisture sensitive element according to the present invention.

In this moisture sensitive element, comb-like opposing electrodes 102 are formed in a central portion of the upper surface of an alumina substrate 101. A functional film 103 is so formed as to substantially cover the opposing electrodes. This functional film 103 is impregnated with an aqueous solution of lithium chloride as electrolytic salt. A heater 104 and a temperature sensor 105 for measuring the temperature of the substrate 101 are embedded in the center of the substrate 101. These heater 104 and temperature sensor 105 are arranged below the opposing electrodes 102. Connecting terminals 107a and 107b are formed at the end portions of the opposing electrodes 102 on the substrate 101. Also, terminals 108a and 108b for supplying power to the heater 104 and terminals 109a and 109b connected to the temperature sensor 105 are formed on the substrate 101. Lead wires 111a, 111b, 112a, 112b, 113a, and 113b are connected to these terminals by using a conductive adhesive or solder. These lead wires are connected to a power supply and a computer (neither is shown).

Note that the material of the substrate 101 can also be ceramics.

As the substrate 101, it is possible to use, e.g., a 6×50-mm, 2-mm thick alumina substrate. In FIG. 2, the narrower portion is shown in an enlarged scale for illustrative convenience. The opposing electrodes 102 are formed by a well-known print-wiring technology and have a width of 0.15 mm, and a distance d between the teeth is about 0.10 mm.

The characteristics of the temperature sensor 105 are 25 Ω±20% (at 23° C.) and T.C.R. 4,440 ppm/° C. (23 to 800° C.), and the heater specifications are DC 12V and 500±50° C.

Figure 3:
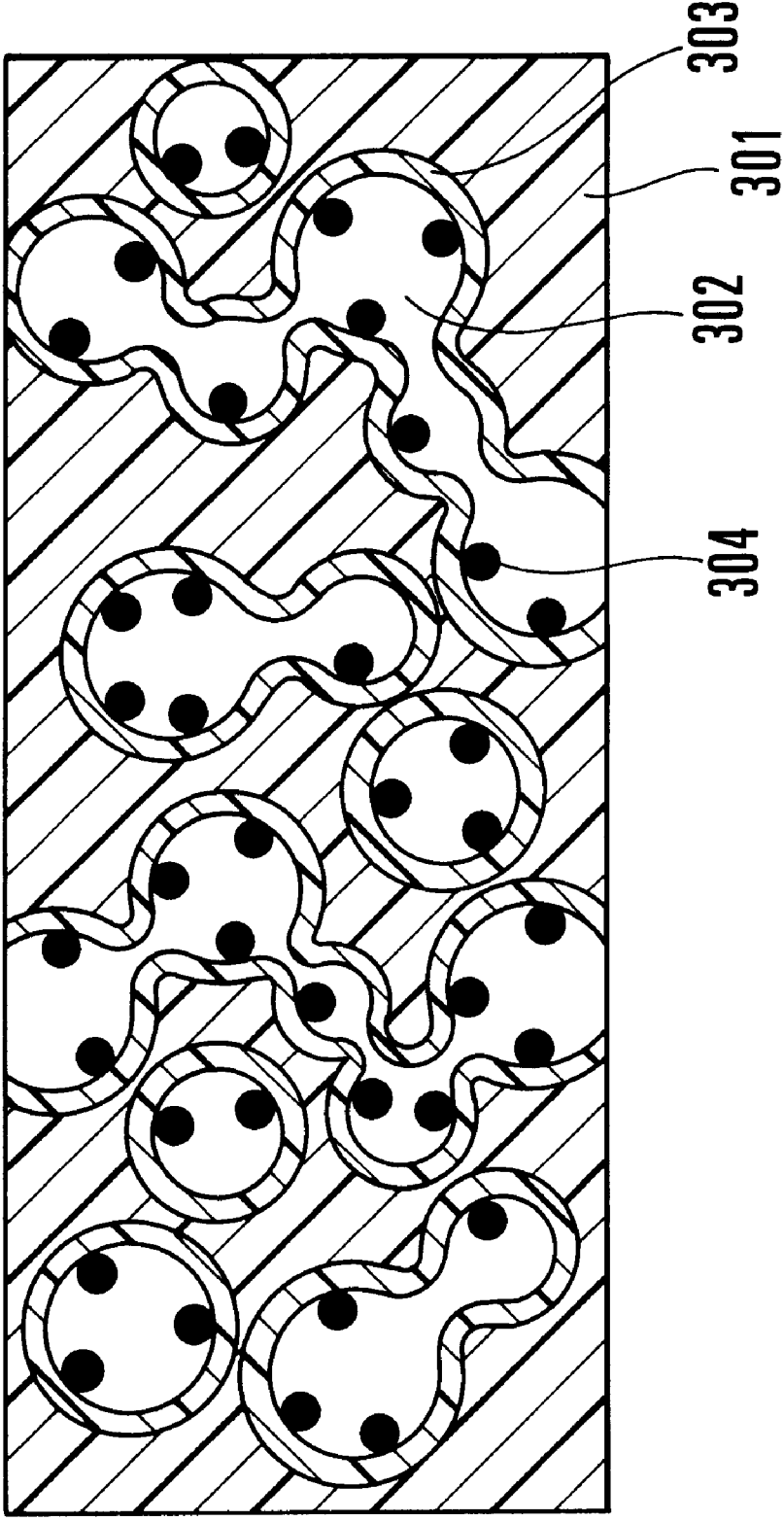
FIG. 3 is a sectional view showing part of the structure of a functional film.

The functional film 103 will be described in more detail below. As shown in FIG. 3, the functional film 103 of this embodiment is a porous film 301 made from a hydrophilic polymer material such as polyvinyl alcohol. In addition, a film (holding film) 303 made from a hydrophobic polymer material such as polyvinyl acetate is formed on the inner walls of a large number of pores 302 formed in the film 301. This film 303 can also be considered as a mixture of the hydrophilic and hydrophobic polymer materials. The strength of the film 301 can be increased by the use of the film 303.

When this porous film 301 of the hydrophilic polymer material is impregnated with an aqueous lithium chloride solution having a predetermined concentration, lithium chloride 301 is held in the pores 302 to form the functional film 103.

As described above, in the functional film 103, a plurality of fine pores are porously formed in the hydrophilic polymer material film. Therefore, an aqueous solution can be held in these fine pores without flowing out from these pores. Additionally, the hydrophobic polymer material film is formed on the inner walls of the pores. This prevents the hydrophilic polymer material from being eluted although an aqueous solution is held in these pores.

Consequently, an aqueous solution of lithium chloride is held in the pores of the porous structure of the functional film 103 impregnated with this aqueous lithium chloride solution without flowing out from these pores.

In actual use, the aqueous lithium chloride solution held in the pores of the porous structure of the functional film 103 is used in a state in which a moisture amount is decreased to such an extent that lithium chloride precipitates. If this functional film 103 is left to stand for long time periods in a high-temperature, high-humidity atmosphere, lithium chloride absorbs moisture in the pores of the porous structure of the functional film 103. Consequently, the concentration of the aqueous solution held in these pores decreases, and this decreases the viscosity. Even if the concentration of the held aqueous lithium chloride solution thus decreases, the aqueous lithium chloride solution can be kept held because, as described above, the base of the functional film 103 is made from a hydrophilic polymer material and so a hydrophilic group exists on the surface of the film.

The size of the pores constituting the porous structure of the functional film 103 can be about 0.01 to 1 $\mu$m. If the pore size is smaller than these values, the result is a bulk structure which is not essentially porous, and it is no longer possible to impregnate a film made from a hydrophilic polymer material with an aqueous solution. On the other hand, if the pore size is too large, a film made from a hydrophilic polymer material cannot be formed any longer.

Also, if the film thickness of the functional film 103 is too small, no stable film can be obtained while a porous structure is maintained. If the film thickness is too large, water vapor or moisture does not easily penetrate into the whole film. This lowers the response speed of the moisture sensitive element and produces hysteresis. For these reasons, an optimum film thickness of the functional film 103 is 0.1 to 20 $\mu$m.

A method of manufacturing the functional film 103 will be described below.

This method will be explained by taking polyvinyl alcohol and polyvinyl acetate as examples of the hydrophilic polymer material and the hydrophobic polymer material, respectively.

Figure 4:
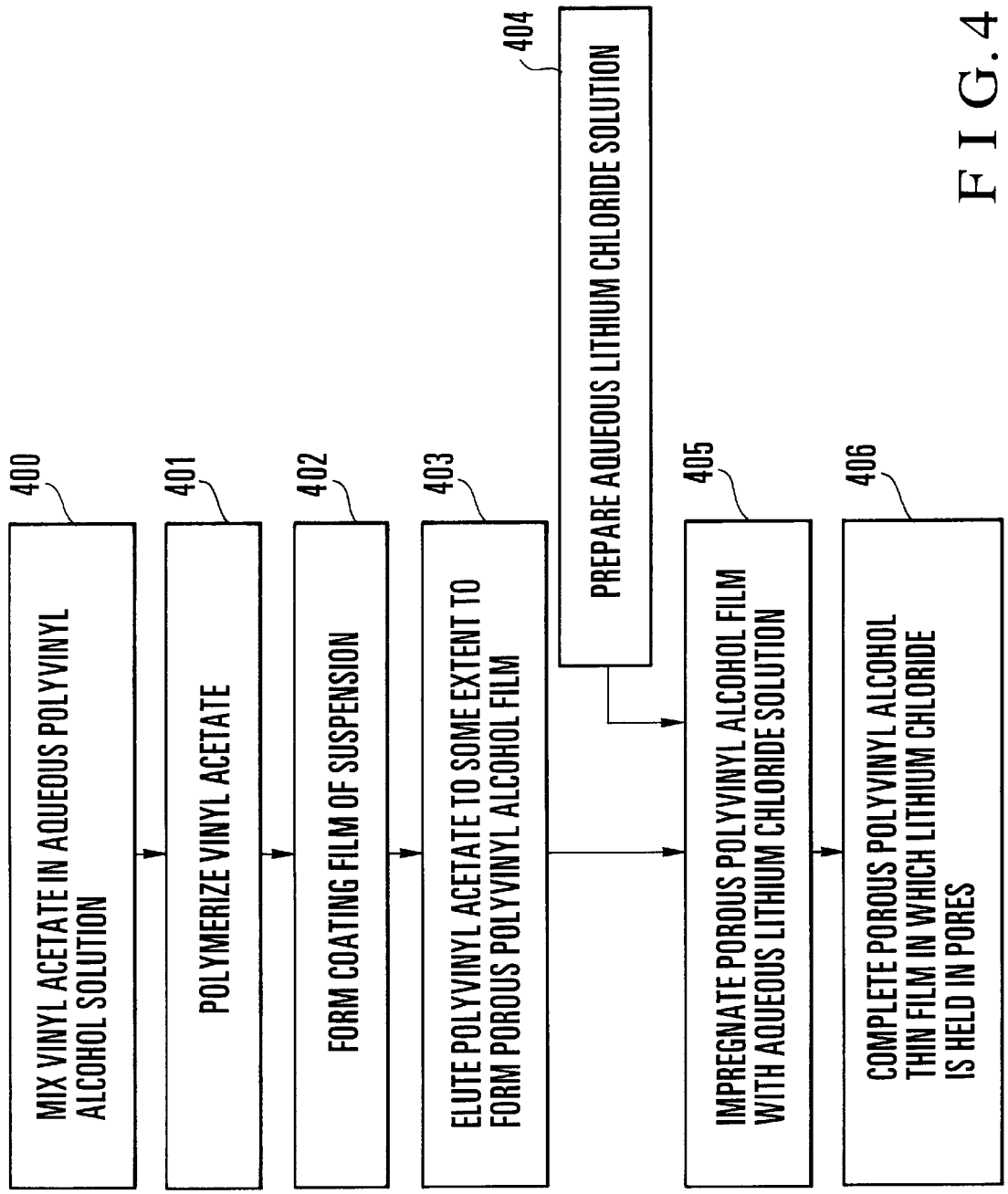
FIG. 4 is a flow chart showing the procedure of a method of manufacturing the functional film.

As shown in the flow chart of FIG. 4, in step 400, vinyl acetate is mixed in an aqueous solution of polyvinyl alcohol to prepare an emulsion.

In step 401, vinyl acetate is polymerized while the mixed solution is stirred. An inhibitor for inhibiting copolymerization can also be added during the polymerization so that polyvinyl alcohol and vinyl acetate do not copolymerize.

In step 402, a predetermined region of a predetermined substrate is coated with an aqueous polyvinyl alcohol solution (suspension) in which vinyl acetate is polymerized to form polyvinyl acetate. This coating film is dried to some extent by heating at about 50° C. As shown in FIG. 2, predetermined electrode wires are formed on this substrate.

In step 403, the coating film is dipped into a solvent such as acetone to elute polyvinyl acetate in the coating film to a certain degree (an elution ratio of 55 to 75%), thereby forming a porous polyvinyl alcohol thin film.

Meanwhile, in step 404, lithium chloride is dissolved in water to prepare an aqueous lithium chloride solution having a predetermined concentration.

In step 405, the coating film treated in step 403 is dipped into the aqueous lithium chloride solution prepared in step 404. Consequently, the coating film (porous PVA thin film) in which a plurality of pores are porously formed is impregnated with the aqueous lithium chloride solution.

As a result of the above procedure, a porous polymer film (functional film) in which lithium chloride is held in polyvinyl alcohol in which a plurality of pores are porously formed on the substrate, and this completes a moisture sensitive element using lithium chloride (step 406).

The formation of the porous structure of the polyvinyl alcohol film will be described in more detail below.

First, vinyl acetate is added to an aqueous solution of polyvinyl alcohol, and the resultant mixture is well stirred to disperse vinyl acetate, thereby preparing an emulsion. A predetermined emulsifying agent can also be added during the preparation. Alternatively, vinyl acetate can be dispersed by irradiation of ultrasonic waves. It is expected that the size of droplets of vinyl acetate can be decreased by the use of ultrasonic waves.

A polymerization initiator is added to the emulsion, and the resultant material is heated to a predetermined temperature to polymerize vinyl acetate. The result is a suspension in which fine grains of polyvinyl acetate are dispersed in the aqueous polyvinyl alcohol solution.

Figure 5A:
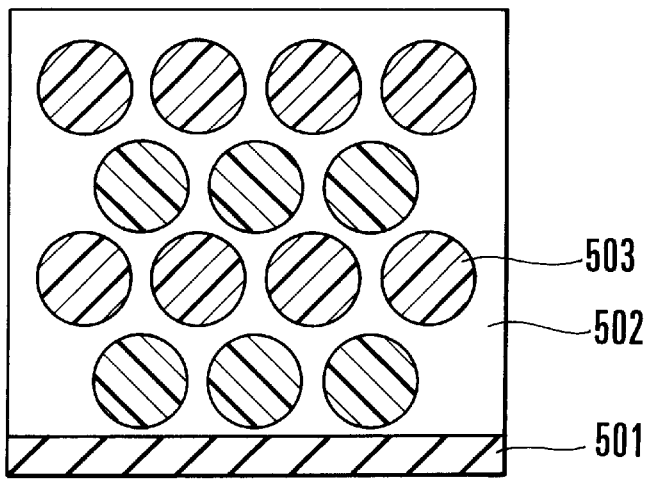
FIGS. 5A to 5C are views for explaining the method of manufacturing the functional film.

As shown in FIG. 5A, the surface of a predetermined substrate 501 is coated with this suspension. Consequently, fine grains 503 of polyvinyl acetate are dispersed in the polyvinyl alcohol film 502 on the substrate 501.

Figure 5B:
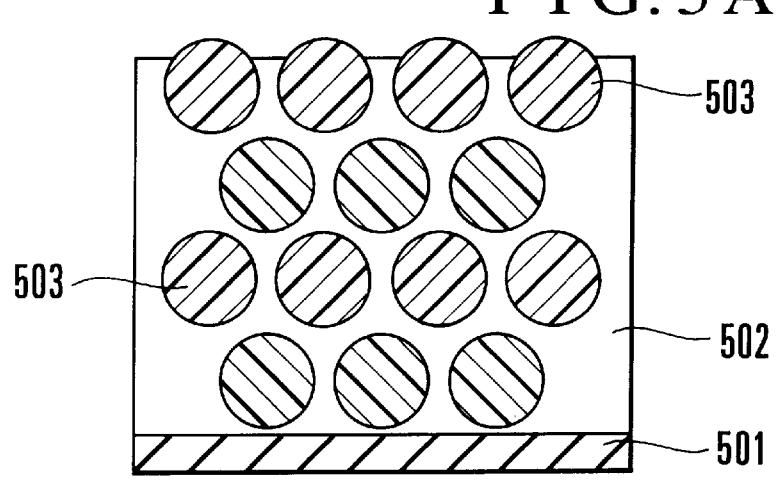

When this coating film is dried to some extent to reduce the volume of the polyvinyl alcohol film 502, as shown in FIG. 5B, some of the fine grains 503 of polyvinyl acetate are exposed to the surface of the polyvinyl alcohol film.

Figure 5C:
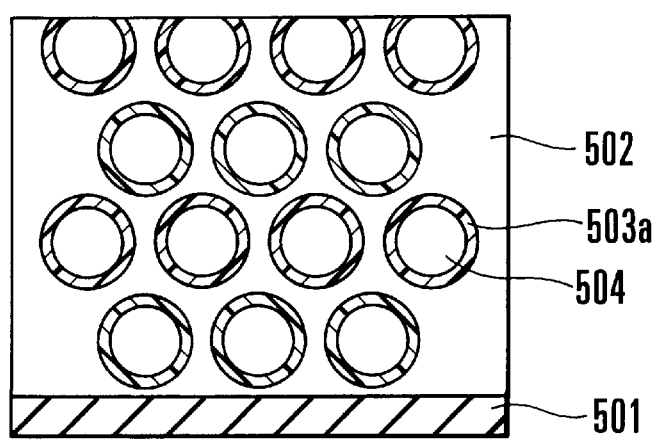

The film in this state and the substrate 501 are together dipped into acetone for a predetermined time. Since only polyvinyl acetate is eluted to acetone, the grains 503 are hollowed. That is, as shown in FIG. 5C, a porous state (porous structure) in which a holding film 503a made from polyvinyl acetate is formed on the inner walls of pores 504 is formed in the polyvinyl alcohol film 502 on the substrate 501.

The amount of vinyl acetate to be mixed in an aqueous solution of polyvinyl alcohol is about polyvinyl alcohol:vinyl acetate =1:10 to 3:10 as a weight ratio. If the component ratio of vinyl alcohol is too small, the film itself cannot be formed. If the component ratio of vinyl acetate is smaller than the above component ratio, no desired porous structure can be obtained. That is, if the component ratio of vinyl acetate is increased, a formable pore size is increased to make the formation of the film impossible. On the other hand, if the component ratio of vinyl acetate is decreased, a formable pore size is decreased. If the component ratio of vinyl acetate is further decreased, the number of pores to be formed is also decreased. Consequently, no porous structure can be obtained. When the mixing ratio of vinyl acetate is about polyvinyl alcohol:vinyl acetate=1:10 to 3:10 as a weight ratio, the size of each pore of a formable porous structure is about 0.01 to 1 $\mu$m.

Also, if the time of dipping into acetone for eluting polyvinyl acetate is too long, polyvinyl acetate is completely eluted. That is, if polyvinyl acetate is too eluted, almost no polyvinyl acetate holding film is formed on the inner walls of a plurality of pores in the porous polyvinyl alcohol film 502, so no water resistance can be obtained. On the other hand, if the amount of elution is too small, no sufficient pores can be formed in the grains of polyvinyl acetate, so no porous structure can be obtained. As described above, therefore, the elution amount of polyvinyl acetate is preferably about 55 to 75% as an elution ratio. A mixing ratio after the porous structure is formed is preferably polyvinyl alcohol:polyvinyl acetate=6:5 to 6:27.

When, however, the strength such as the water resistance of the polyvinyl alcohol porous film can be more or less sacrificed, the elution amount of polyvinyl acetate can also exceed 75% as an elution ratio.

In the above embodiment, polyvinyl alcohol is used as the hydrophilic polymer material. However, it is also possible to use a natural polymer such as gelatin, tragacanth, starch, methyl cellulose, CMC (carboxymethyl cellulose), or a derivative of a natural polymer and a synthetic polymer such as PVA, partially saponified PVA, another vinyl alcohol copolymer, or polyacrylate.

The hydrophobic polymer material is also not limited to polyvinyl acetate (vinyl acetate). For example, polystyrene (styrene), ethylene polychloride (ethylene dichloride), or polyvinyl benzene (divinylbenzene) can be used.

Also, the electrolytic salt is not limited to lithium chloride, and some other salt such as calcium chloride can be used. However, lithium chloride is one of inorganic compounds having the highest moisture absorption, and the vapor pressure of an aqueous solution of lithium chloride is relatively lower than those of other salts such as calcium chloride. In addition, the solidification point of the aqueous solution is also low. Furthermore, lithium chloride has another advantage that it is very easy to handle.

As has been described above, the moisture sensitive element of the present invention is a moisture sensitive element comprising a functional film formed in contact with opposing electrodes arranged on a substrate, and temperature measuring means for measuring a temperature of the functional film, wherein the functional film has a porous structure made from a first polymer material having hydrophilic nature and including a plurality of fine pores, and comprises a holding film formed on inner walls of the pores and made from a second polymer material having hydrophobic nature, and electrolytic salt held in the pores.

Accordingly, the electrolytic salt is confined in a plurality of fine pores in which a hydrophilic group exists. Meanwhile, moisture can freely enter and leave in portions where the electrolytic salt exists. That is, even when the electrolytic salt absorbs moisture to form an aqueous solution, this solution is prevented from flowing out from the functional film. As a consequence, the moisture sensitive element of the present invention can stably operate over long time periods.

Also, in the method of manufacturing the moisture sensitive element according to the present invention, the functional film is formed as follows: That is, a base solution is formed by dissolving a first polymer material having hydrophilic nature in a first solvent having a polarity and capable of dissolving the first polymer material. An emulsion is formed by dispersing a hydrophobic organic material, which is not dissolved in the first solvent, in the base solution. The organic material dispersed in the form of droplets in the emulsion is polymerized to form a suspension in which grains of a second polymer material, which is obtained by the polymerization of the organic material and has hydrophobic nature, are dispersed in the base solution. A coating film is formed by coating a predetermined region on the substrate with the suspension. Moisture in the coating film is partially removed to expose some of the grains to a surface of the coating film. The second polymer material is dissolved by dipping the coating film into a second solvent which does not dissolve the first polymer material and dissolves the second polymer material, thereby forming a porous film by giving the coating film a porous structure having a large number of pores on inner walls formed with a film made from the second polymer material. The porous film is dipped into an aqueous solution of electrolytic salt to impregnate the porous film with the aqueous solution of electrolytic salt, thereby holding the electrolytic salt in the pores constituting the porous film.

That is, a film made from the first polymer material is given a porous structure, and the electrolytic salt is held in a plurality of pores of the porous structure. Since the first polymer material is hydrophilic, even when the electrolytic salt absorbs moisture to form an aqueous solution, this solution can be held. Accordingly, the electrolytic salt is prevented from flowing out from the functional film. As a consequence, the moisture sensitive element of the present invention can stably operate over long time periods.

What is claimed is:

1. A moisture sensitive element comprising a functional film formed in contact with opposing electrodes arranged on a substrate, and temperature measuring means for measuring a temperature of said functional film, wherein said functional film has a porous structure made from a first polymer material having hydrophilic nature and including a plurality of fine pores, and comprises a holding film formed on inner walls of said pores and made from a second polymer material having hydrophobic nature, and electrolytic salt held in said pores.

2. An element according to claim 1, wherein an average pore size of said pores constituting said porous structure is 0.01 to 3 $\mu$m.

3. An element according to claim 1, wherein a film thickness of said functional film is 0.1 to 20 $\mu$m.

4. An element according to claim 1, wherein a component weight ratio of said first polymer material to said second polymer material is 6:5 to 6:27.

5. An element according to claim 1, wherein said first polymer material is polyvinyl alcohol.

6. An element according to claim 1, wherein said second polymer material is polyvinyl acetate.

* * * * *

UNITED STATES PATENT AND TRADEMARK OFFICE
CERTIFICATE OF CORRECTION

PATENT NO. : 6,126,312
DATED : October 3, 2000
INVENTOR(S) : Sakei et al.

It is certified that error appears in the above-identified patent and that said Letters Patent is hereby corrected as shown below:

Title page,
Item [56], References Cited, FOREIGN PATENT DOCUMENTS, after "2/1974 Germany" insert the Class and Subclass numbers -- G01N 27/12 --; and delete "26 10 266 3/1976 Germany G01N 27/14".

Signed and Sealed this

Thirteenth Day of September, 2005

JON W. DUDAS
*Director of the United States Patent and Trademark Office*